US012611086B2

(12) United States Patent
Meglan et al.

(10) Patent No.: US 12,611,086 B2
(45) Date of Patent: Apr. 28, 2026

(54) SYSTEMS AND METHODS FOR MACHINE READABLE IDENTIFICATION OF SURGICAL TOOLS IN-SITU

(71) Applicant: Covidien LP, Mansfield, MA (US)

(72) Inventors: Dwight Meglan, Westwood, MA (US); Eric J. Taylor, Southington, CT (US)

(73) Assignee: Covidien LP, Mansfield, MA (US)

( * ) Notice: Subject to any disclaimer, the term of this patent is extended or adjusted under 35 U.S.C. 154(b) by 614 days.

(21) Appl. No.: 17/790,806

(22) PCT Filed: Dec. 22, 2020

(86) PCT No.: PCT/US2020/066506

§ 371 (c)(1),
(2) Date: Jul. 5, 2022

(87) PCT Pub. No.: WO2021/158305

PCT Pub. Date: Aug. 12, 2021

(65) Prior Publication Data

US 2023/0036858 A1 Feb. 2, 2023

Related U.S. Application Data

(60) Provisional application No. 62/969,745, filed on Feb. 4, 2020.

(51) Int. Cl.
*A61B 1/00* (2006.01)
*A61B 1/04* (2006.01)
*A61B 1/06* (2006.01)

(52) U.S. Cl.
CPC ........ *A61B 1/000094* (2022.02); *A61B 1/046* (2022.02); *A61B 1/0638* (2013.01)

(58) Field of Classification Search
CPC .. A61B 1/000094; A61B 1/046; A61B 1/0638
See application file for complete search history.

(56) References Cited

U.S. PATENT DOCUMENTS

| 5,820,545 A | 10/1998 | Arbter et al. |
| 6,132,368 A | 10/2000 | Cooper |

(Continued)

FOREIGN PATENT DOCUMENTS

| EP | 3031386 A1 | 6/2016 |
| KR | 20010027541 A | 4/2001 |

(Continued)

OTHER PUBLICATIONS

Collins Dictionaries, editor. "Mark1." Collins English Dictionary, 12th ed., Collins, 2014. Credo Reference, https://search.credoreference.com/articles/Qm9va0FydGljbGU6MzYxMDM0Ng==?aid=279753. (Year: 2014).*

(Continued)

*Primary Examiner* — Amandeep Saini
*Assistant Examiner* — Caroline Tabancay Duffy
(74) *Attorney, Agent, or Firm* — Carter, DeLuca & Farrell LLP

(57) ABSTRACT

A method for object detection in endoscopy images includes capturing an image of an object, by an imaging device, the image including a first light and/or a second light radiating from the object. The object includes an infrared (IR) marking. The method further includes accessing the image, performing real time image recognition on the image to detect the IR marking, performing real time image recognition on the image to detect the object and classify the object, based on the IR marking, generating an augmented image based on removing the IR marking from the image, and displaying the augmented image on a display.

20 Claims, 5 Drawing Sheets

700

(56)     References Cited

U.S. PATENT DOCUMENTS

| | | | |
|---|---|---|---|
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,930,065 B2 | 4/2011 | Larkin et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |

(56)                 References Cited

U.S. PATENT DOCUMENTS

| | | | |
|---|---|---|---|
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,498,231 B2 | 11/2016 | Haider et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |

(56) References Cited

U.S. PATENT DOCUMENTS

| | | | |
|---|---|---|---|
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Piolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 2006/0258938 A1 | 11/2006 | Hoffman et al. | |
| 2010/0168562 A1* | 7/2010 | Zhao | A61B 34/30 600/426 |
| 2011/0090343 A1* | 4/2011 | Alt | G06T 19/006 348/E5.085 |
| 2015/0077529 A1 | 3/2015 | Hatta et al. | |
| 2016/0074128 A1* | 3/2016 | Dein | A61B 50/362 600/424 |
| 2016/0203602 A1* | 7/2016 | Hayashi | A61B 1/0638 382/128 |
| 2017/0305016 A1 | 10/2017 | Larkin et al. | |
| 2019/0083180 A1* | 3/2019 | Ichiki | G06T 7/0012 |
| 2019/0205630 A1* | 7/2019 | Kusens | A61B 5/6891 |
| 2020/0138518 A1* | 5/2020 | Lang | A61B 17/1666 |
| 2020/0193236 A1* | 6/2020 | Oosake | G06V 10/454 |
| 2022/0061929 A1* | 3/2022 | Tao | G01B 9/02091 |

FOREIGN PATENT DOCUMENTS

| | | |
|---|---|---|
| KR | 20120122643 A | 11/2012 |
| WO | 2018140646 A1 | 8/2018 |

OTHER PUBLICATIONS

Editors of the American Heritage Dictionaries (Ed.). (2016). Track. In The American Heritage(R) Dictionary of the English Language (6th ed.). Houghton Mifflin. https://search.credoreference.com/ articles/Qm9va0FydGljbGU6NDQ5ODI2OA==?aid=279753 (Year: 2016).*

International Search Report mailed Mar. 16, 2021 and Written Opinion completed Mar. 8, 2021 corresponding to counterpart Int'l Patent Application PCT/US2020/066506.

* cited by examiner

SYSTEMS AND METHODS FOR MACHINE READABLE IDENTIFICATION OF SURGICAL TOOLS IN-SITU

CROSS-REFERENCE TO RELATED APPLICATIONS

The present application is a U.S. National Stage Application filed under 35 U.S.C. § 371 (a) claiming the benefit of and priority to International Patent Application No. PCT/US2020/066506, filed Dec. 22, 2020, which claims the benefit of and priority to U.S. Provisional Patent Application Ser. No. 62/969,745, filed Feb. 4, 2020, the entire disclosures of each of which being incorporated by reference herein.

FIELD

The present disclosure relates to devices, systems and methods for surgical tool identification in images, and more particularly, to machine readable identification of surgical tools in images during surgical procedures.

BACKGROUND

Endoscopes are introduced through an incision or a natural body orifice to observe internal features of a body. Conventional endoscopes are used for visualization during endoscopic or laparoscopic surgical procedures. During such surgical procedures, it is possible for a view of the instrument to be obstructed by tissue or other instruments.

During minimally invasive surgery, and especially in robotic surgery, knowledge of the exact surgical tools appearing in the endoscopic video feed can be useful for facilitating features that enhance the surgical experience. While electrical or wireless communication between something attached/embedded in the tool is a possible means to do this, when this infrastructure is either not available or not possible, another identification means is needed. Accordingly, there is interest in improving imaging technology.

SUMMARY

The disclosure relates to devices, systems, and methods for surgical tool identification in images. In accordance with aspects of the disclosure, a system for object identification in endoscopy images is presented. The system includes a light source, an imaging device, and an imaging device control unit. The light source is configured to provide light within a surgical operative site. The light source is further configured to produce a first light including an infrared (IR) band and a second light configured to produce a visible band. The imaging device is configured to acquire images from the surgical operative site. The imaging device control unit is configured to control the imaging device. The control unit includes a processor and a memory storing instructions. The instructions, when executed by the processor, cause the system to capture an image of an object located in the surgical operative site, by the imaging device. The instructions further cause the system to access the image, perform real-time image recognition on the image to detect the IR marking, perform real-time image recognition on the image to detect the object and classify the object, based on the IR marking, generate an augmented image based on removing the IR marking from the image; and display the augmented image on a display. The image includes the first light and the second light radiating from the object. The object includes an infrared (IR) marking.

In an aspect of the present disclosure, performing real-time image recognition, based on the IR marking, may include amplifying the IR marking.

In another aspect of the present disclosure, the instructions, when executed, may further cause the system to: perform real-time image recognition on the image to detect the object and classify the object, based on the second light and compare the object classification based on the amplified IR marking and the object classification based on the second light to produce a classification accuracy value. In a case where the classification accuracy value is above a predetermined threshold, the system may: generate a first bounding box around the detected object, generate a first augmented view of the image based on the classification, the augmented view including the bounding box and a tag indicating the classification, and display the augmented image on a display.

In an aspect of the present disclosure, in a case where the classification accuracy value is below the predetermined threshold, the instructions, when executed, may further cause the system to display on the display an indication that the classification accuracy value is not within an expected range.

In yet another aspect of the present disclosure, the augmented view may further include an indication of the classification accuracy value.

In a further aspect of the present disclosure, the IR marking may include a pattern that indicates a data bit and an error checking bit.

In an aspect of the present disclosure, the data bit may indicate a surgical tool type and/or a surgical tool feature.

In a further aspect of the present disclosure, the instructions may further cause the system to perform tracking of the object based on the IR marking.

In yet another aspect of the present disclosure, the instructions may further cause the system to adjust a control parameter of the system based on the detected object.

In a further aspect of the present disclosure, the IR marking may include a logo, a QR code, a texture, a dot pattern, and/or a unique identifier.

In accordance with aspects of the disclosure, a method of object identification in endoscopy images is presented. The method includes capturing an image of an object within a surgical operative site, by an imaging device. The image includes a first light and a second light radiating from the object, the object including an infrared (IR) marking. The method further includes accessing the image, performing real-time image recognition on the image to detect the IR marking, performing real-time image recognition on the image to detect the object and classify the object, based on the IR marking, generating an augmented image based on removing the IR marking from the image, and displaying the augmented image on a display.

In yet a further aspect of the present disclosure, performing real-time image recognition on the image to detect the IR marking may include amplifying the IR marking.

In yet another aspect of the present disclosure, the method may further include performing real-time image recognition on the image to detect the object and classify the object, based on the second light. The method may further include comparing the object classification based on the amplified IR marking and the object classification based on the second light to produce a classification accuracy value. In a case where the classification accuracy value is above a predetermined threshold, the method further may include: generating a first bounding box around the detected object, generating a first augmented view of the image based on the classification, the augmented view including the bounding box and a tag indicating the classification, and displaying the augmented image on a display.

In a further aspect of the present disclosure, in a case where the classification accuracy value is below the predetermined threshold, the method may further include displaying on the display an indication that the classification accuracy value is not within an expected range.

In yet a further aspect of the present disclosure, the augmented view may further include an indication of the classification accuracy value.

In yet another aspect of the present disclosure, the method may further include performing tracking of the object based on the detected object based on the IR marking.

In a further aspect of the present disclosure, the IR marking may include a logo, a QR code, a texture, a dot pattern, and/or a unique identifier.

In an aspect of the present disclosure, the IR marking may include a pattern that indicates a data bit and/or an error checking bit.

In accordance with aspects of the disclosure, a non-transitory storage medium that stores a program causing a computer to execute a computer-implemented method of object identification in endoscopy images is presented. The computer-implemented method includes capturing an image of an object, by an imaging device, the image including a first light and a second light, the object including an infrared (IR) marking, accessing the image, performing real time image recognition on the image to detect the IR marking, performing real time image recognition on the image to detect the object and classify the object, based on the IR marking, generating an augmented image based on removing the IR marking from the image, and displaying the augmented image on a display.

Further details and aspects of various embodiments of the disclosure are described in more detail below with reference to the appended figures.

BRIEF DESCRIPTION OF THE DRAWINGS

Embodiments of the disclosure are described herein with reference to the accompanying drawings, wherein.

Figure 1:
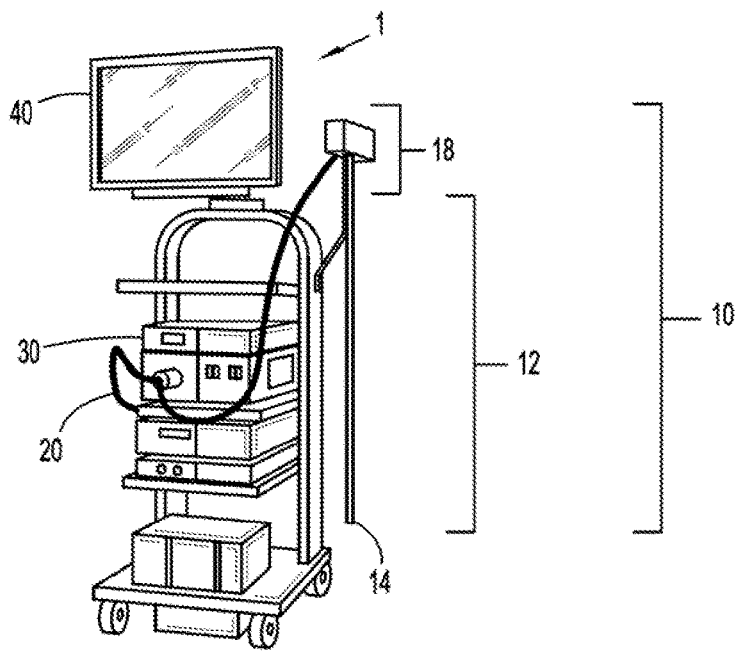
FIG. 1 is a diagram of an exemplary visualization or endoscope system in accordance with the disclosure.

Further details and aspects of exemplary embodiments of the disclosure are described in more detail below with reference to the appended figures. Any of the above aspects and embodiments of the disclosure may be combined without departing from the scope of the disclosure.

DETAILED DESCRIPTION OF EMBODIMENTS

Embodiments of the presently disclosed devices, systems, and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel.

The disclosure is applicable where images of a surgical site are captured. Endoscope systems are provided as an example, but it will be understood that such description is exemplary and does not limit the scope and applicability of the disclosure to other systems and procedures.

Figure 2:
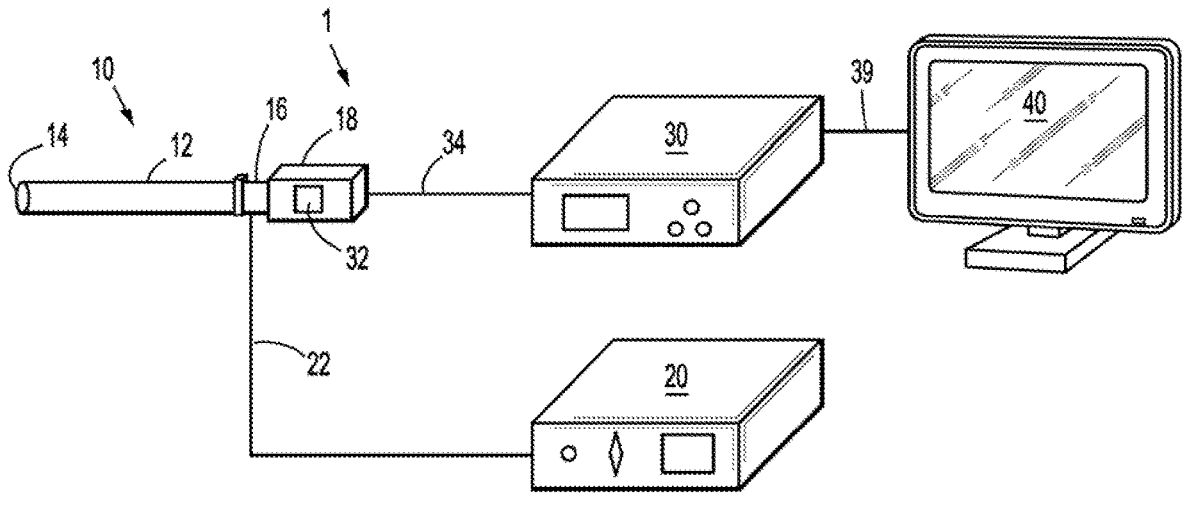
FIG. 2 is a schematic configuration of the visualization or endoscope system of FIG. 1.
Figure 3:
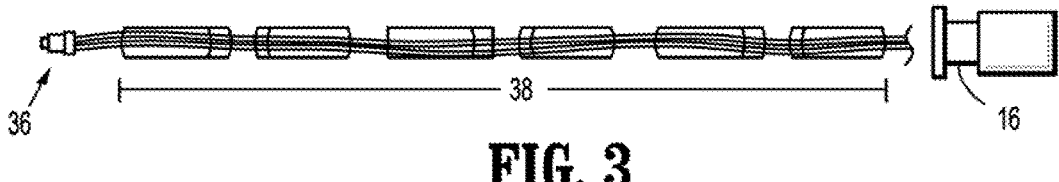
FIG. 3 is a diagram illustrating another schematic configuration of an optical system of the system of FIG. 1.

Referring initially to FIGS. 1-3, an endoscope system 1, in accordance with the disclosure, includes an endoscope 10, a light source 20, a video system 30, and a display device 40. With continued reference to FIG. 1, the light source 20, such as an LED/Xenon light source, is connected to the endoscope 10 via a fiber guide 22 that is operatively coupled to the light source 20 and to an endocoupler 16 disposed on, or adjacent to, a handle 18 of the endoscope 10. The fiber guide 22 includes, for example, fiber optic cable which extends through the elongated body 12 of the endoscope 10 and terminates at a distal end 14 of the endoscope 10. Accordingly, light is transmitted from the light source 20, through the fiber guide 22, and emitted out the distal end 14 of the endoscope 10 toward a targeted internal feature, such as tissue or an organ, of a body of a patient. As the light transmission pathway in such a configuration is relatively long, for example, the fiber guide 22 may be about 1.0 m to about 1.5 m in length, only about 15% (or less) of the light flux emitted from the light source 20 is outputted from the distal end 14 of the endoscope 10.

With reference to FIGS. 2 and 3, the video system 30 is operatively connected to an image sensor 32 mounted to, or disposed within, the handle 18 of the endoscope 10 via a data cable 34. An objective lens 36 is disposed at the distal end 14 of the elongated body 12 of the endoscope 10 and a series of spaced-apart, relay lenses 38, such as rod lenses, are positioned along the length of the elongated body 12 between the objective lens 36 and the image sensor 32. Images captured by the objective lens 36 are forwarded through the elongated body 12 of the endoscope 10 via the relay lenses 38 to the image sensor 32, which are then communicated to the video system 30 for processing and output to the display device 40 via cable 39. The image sensor 32 is located within, or mounted to, the handle 18 of the endoscope 10, which can be up to about 30 cm away from the distal end 14 of the endoscope 10.

With reference to FIGS. 4-7, the flow diagrams include various blocks described in an ordered sequence. However, those skilled in the art will appreciate that one or more blocks of the flow diagram may be performed in a different order, repeated, and/or omitted without departing from the scope of the disclosure. The below description of the flow diagram refers to various actions or tasks performed by one or more video system 30, but those skilled in the art will appreciate that the video system 30 is exemplary. In various embodiments, the disclosed operations can be performed by another component, device, or system. In various embodiments, the video system 30 or other component/device performs the actions or tasks via one or more software applications executing on a processor. In various embodiments, at least some of the operations can be implemented by firmware, programmable logic devices, and/or hardware circuitry. Other implementations are contemplated to be within the scope of the disclosure.

Figure 4:
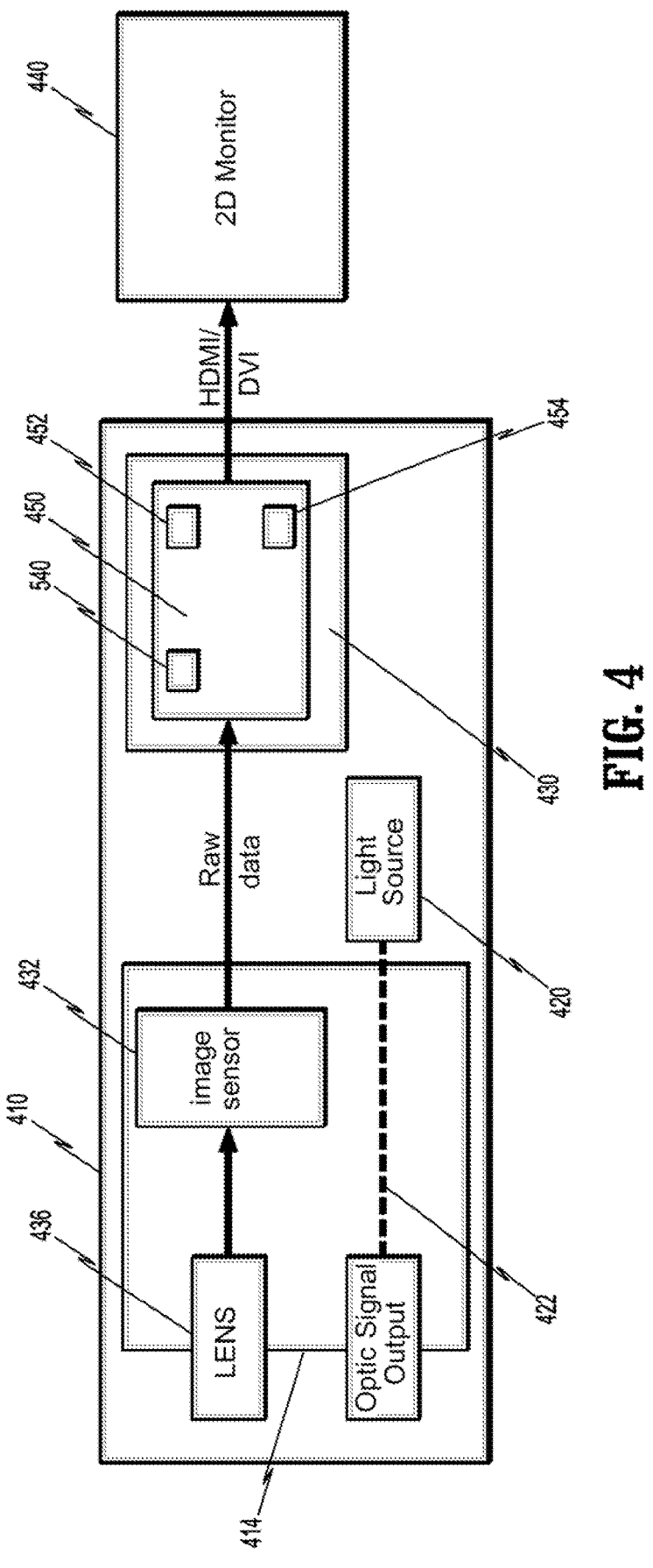
FIG. 4 is a schematic configuration of the visualization or endoscope system in accordance with an embodiment of the disclosure.

Referring to FIG. 4, there is shown a schematic configuration of a system, which may be the endoscope system of FIG. 1 or may be a different type of system (e.g., visualization system, etc.). The system, in accordance with the disclosure, includes an imaging device 410, a light source 420, a video system 430, and a display device 440. The light source 420 is configured to provide light to a surgical site through the imaging device 410 via the fiber guide 422. The distal end 414 of the imaging device 410 includes an objective lens 436 for receiving or capturing the image at the surgical site. The objective lens 436 forwards or transmits the image to the image sensor 432. The image is then communicated to the video system 430 for processing. The video system 430 includes an imaging device controller 450 for controlling the endoscope and processing the images. The imaging device controller 450 includes a processor 452 connected to a computer-readable storage medium or a memory 454 which may be a volatile type memory, such as RAM, or a non-volatile type memory, such as flash media, disk media, or other types of memory. In various embodiments, the processor 452 may be another type of processor such as, without limitation, a digital signal processor, a microprocessor, an ASIC, a graphics processing unit (GPU), field-programmable gate array (FPGA), or a central processing unit (CPU).

In various embodiments, the memory 454 can be random access memory, read only memory, magnetic disk memory, solid state memory, optical disc memory, and/or another type of memory. In various embodiments, the memory 454 can be separate from the imaging device controller 450 and can communicate with the processor 452 through communication buses of a circuit board and/or through communication cables such as serial ATA cables or other types of cables. The memory 454 includes computer-readable instructions that are executable by the processor 452 to operate the imaging device controller 450. In various embodiments, the imaging device controller 450 may include a network interface 540 to communicate with other computers or a server.

Figure 5:
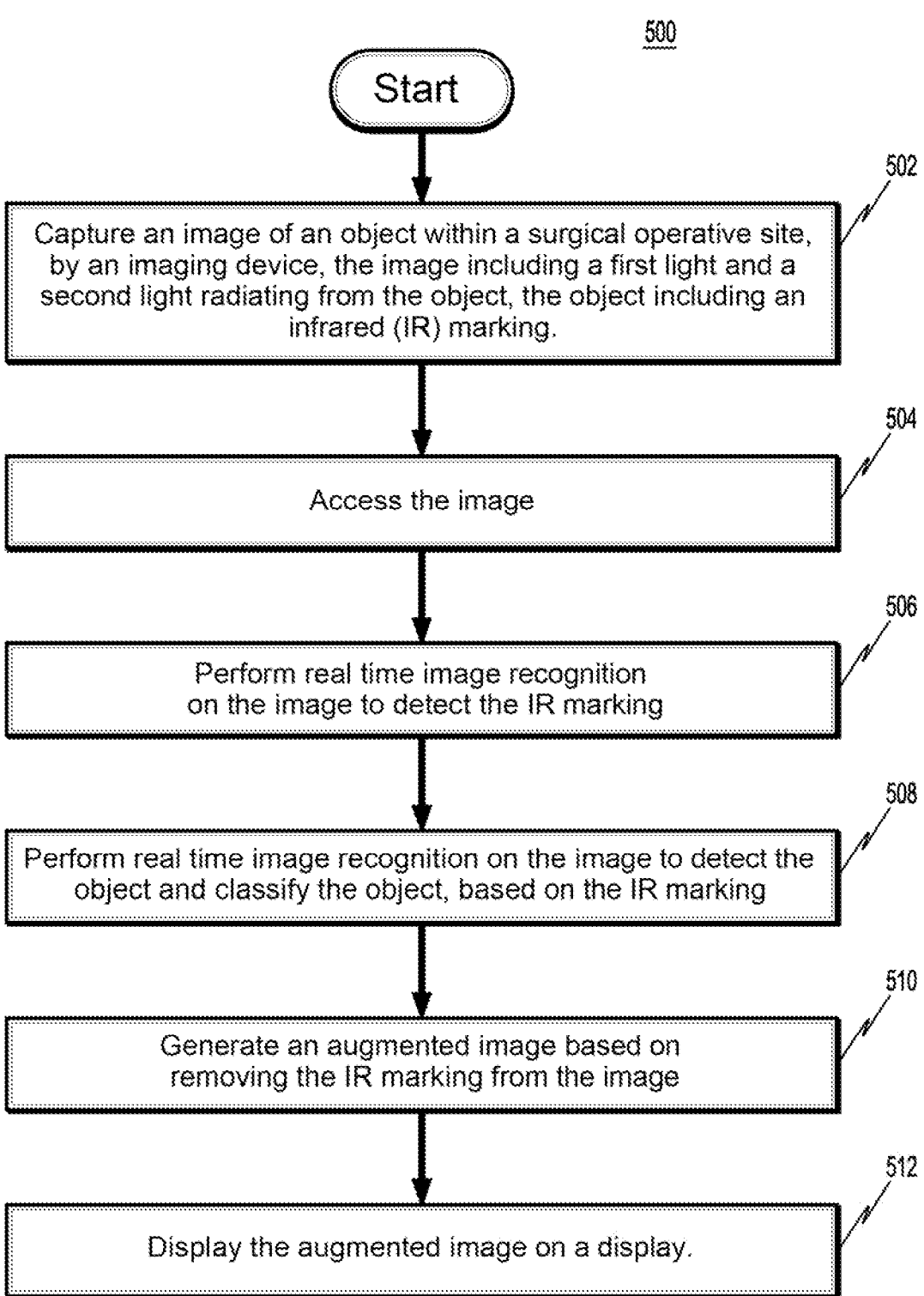
FIG. 5 is a flowchart of a method for object detection in endoscopy images in accordance with an exemplary embodiment of the disclosure.

Referring now to FIG. 5, there is shown an operation for object detection in endoscopy images. In various embodiments, the operation of FIG. 5 can be performed by an endoscope system 1 described above herein. In various embodiments, the operation of FIG. 5 can be performed by another type of system and/or during another type of procedure. The following description will refer to an endoscope system, but it will be understood that such description is exemplary and does not limit the scope and applicability of the disclosure to other systems and procedures.

Initially at step 502, an image of a surgical site is captured via the objective lens 36 and forwarded to the image sensor 32 of endoscope 10 of endoscope system 1. The term "image" as used herein may include still images or moving images (for example, video). The image includes a first light (e.g., infrared) and a second light (e.g., visible light). For example, two light sources may be present to illuminate the surgical site for the endoscope system 1. One light source may be a broad-spectrum white light whose wavelengths would be blocked so that they do not go above the visible range of about 740 nm. The other light source may be purely near infrared, typically anywhere between about 780 nm and 850 nm. It is contemplated that the first light and the second light may be used simultaneously or in any order.

In various embodiments, the image sensor 32 of endoscope 10 may include CMOS sensors. In various embodiments, the CMOS sensors would not have an IR blocking filter on them. When the endoscope is run with the white light, the endoscope 10 would produce normal visible light images. Periodically the light source may be switched to IR only and the markings on the tools imaged. When this IR imaging mode occurs, the image may not be shown to the surgical robot user. For example, the IR image may be used by a robot control system so that it may make use of knowledge of the tool types being used in the surgery at that time.

In various embodiments, when indocyanine green (ICG)-based fluorescence based imaging is needed, the system may include a mode that would allow the visible light and IR lighting to be on simultaneously with the visible light component considerably reduced in its illumination intensity. ICG based imaging uses near infrared light to add contrast to tissue imaging during surgical procedures. In various embodiments, the markings on the tools will be visible in this mode and the primary focus is on when tissue shows it is perfused. In various embodiments, the markings are not too bright relative to the perfusion. In various embodiments, the system may retune the IR wavelength for the marking dye. For example, the ICG IR light could be at 785 nm whereas the marking IR could be above 850 nm. In this way, the marking IR light would not stimulate the ICG and vice versa. In various embodiments, the endoscope 10 and/or endoscope system 1 may include multiple IR sources.

In various embodiments, the captured image is communicated to the video system 30 for processing. For example, during an endoscopic procedure a surgeon may cut tissue with an electrosurgical instrument. When the image is captured, it may include objects such as the tissue and the instrument. In various embodiments, the object may include an infrared (IR) readable marking. For example, the IR marking may be located on the shaft of the instrument. In various embodiments, the IR marking may be disposed on the jaws of the surgical tool. In various embodiments, the IR marking may include a pattern that indicates a data bit and an error checking bit. In various embodiments, the data bit indicates a surgical tool type and/or a surgical tool feature. In various embodiments, the IR marking may include, for example a logo, a QR code, a texture, a dot pattern, and/or a unique identifier. At step 504, the video system 30 accesses the image for further processing.

At step 506, the video system 30 performs real-time image recognition on the image to detect the IR marking. In various embodiments, the video system 30 may amplify the IR marking. In various embodiments, markings may be disposed on the shaft and/or jaws of the robotic surgery tools using near infrared (IR) reflective or fluorescing printing ink. In various embodiments, information about the tools may be seen by an appropriately equipped endoscope but are not visible to those using the system. In various embodiments, CMOS imagers which may be used in endoscopes are sensitive to IR and usually have filters to block from receiving this to prevent the image from being skewed by light not visible to the human eye. Since there is generally no light present within the body, all illumination needs to be added by the endoscope system, e.g., it is not natural light which contains IR. Thus, the added light provided with the endoscope 10 can be designed to not contain any IR light so the IR rejection filter does not need to be present. Thus, the endoscope 10 will be sensitive to IR. In various embodiments, by occasionally introducing IR into the illumination system and then blanking that image from being shown to the robotic surgery system users, the information about the tools can be observed without the users being aware of what is taking place. In various embodiments, if the IR wavelength needed for the ink is tuned to the same one used for activating indocyanine green dye (ICG), which is may be used to observe perfusion during surgery, then the same ICG capability that may be built into the endoscope can be leveraged. For example, this wavelength may be in the range of about 785 nm.

At step 508, the video system 30 performs real time image recognition on the image to detect the object and classify the object, based on the IR marking. In various embodiments, the encoding system may be self-testable to ensure that complete information has been read. For example, similar to how CRC numbers are used to check computer information transmissions and how QR Codes can be queried about the correctness of what was read. In various embodiments, a checksum or a hash code may be used to ensure complete information has been read. At step 510, the video system 30 generates an augmented image where the IR marking is removed from the image.

At step 512, the video system 30 displays the augmented image on a display for the operator to see. In various embodiments, the video system 30 may perform tracking of the object based on the detected object based on the IR marking. In various embodiments, the video system 30 may adjust control parameters of the system based on the detected object. In various embodiments, the video system 30 may perform tracking of the object based on the detected object based on the IR marking.

Figure 6:
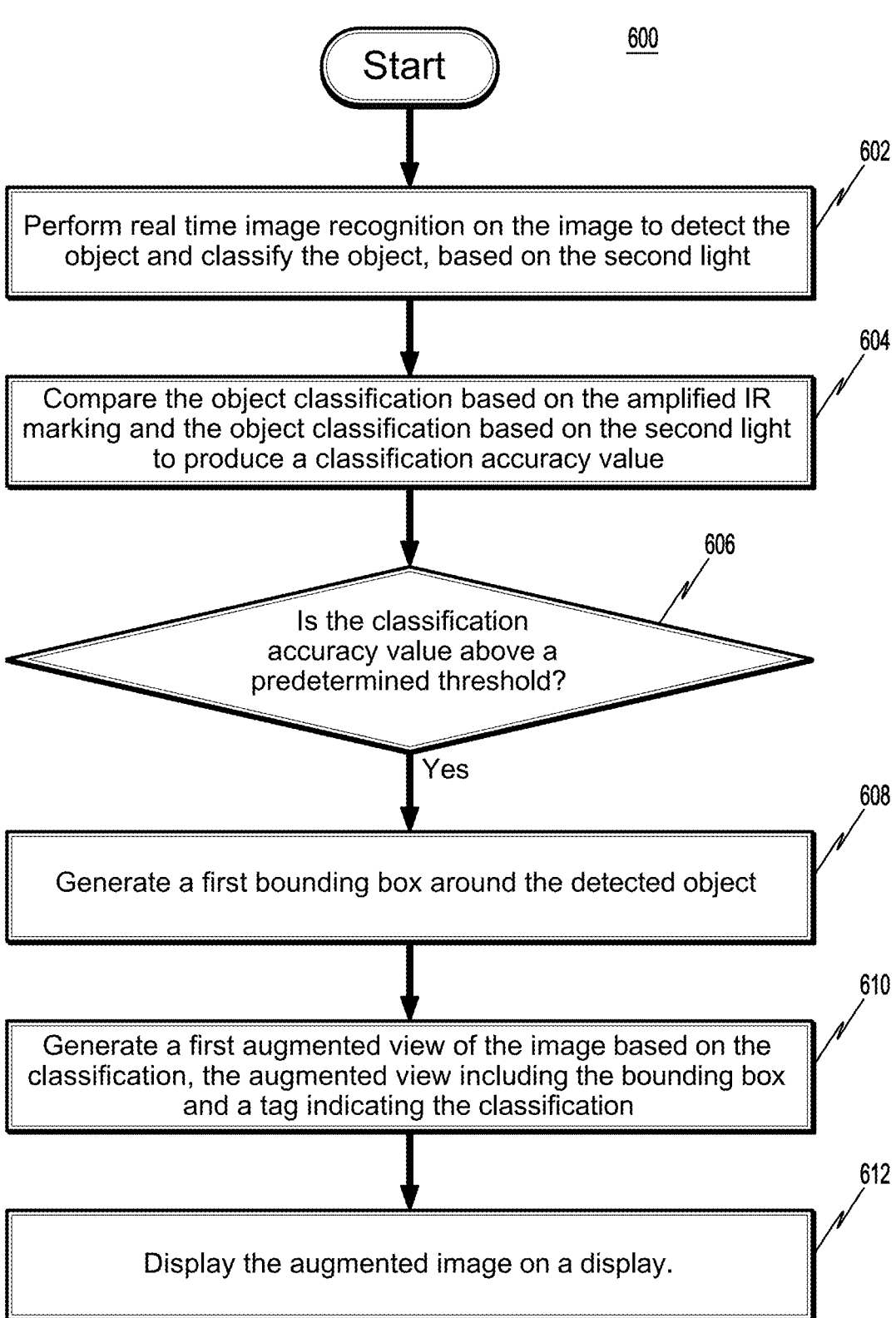
FIG. 6 is a flowchart of a method for object detection in endoscopy images in accordance with an exemplary embodiment of the disclosure.

Referring now to FIG. 6, there is shown an operation for object detection in endoscopy images. In various embodiments, the operation of FIG. 6 can be performed by an endoscope system 1 described above herein. In various embodiments, the operation of FIG. 6 can be performed by another type of system and/or during another type of procedure. The following description will refer to an endoscope system, but it will be understood that such description is exemplary and does not limit the scope and applicability of the disclosure to other systems and procedures.

Initially, at step 602, the video system 30 performs real time image recognition on the image to detect the object and classify the object, based on the second light. For example, the video system 30 may detect a surgical tool based on the visible light and may classify it as a bipolar grasper.

At step 604, the video system 30 compares the object classification based on the amplified IR marking and the object classification based on the second light to produce a classification accuracy value. For example, the object may be classified as a bipolar grasper based on the amplified IR marking, and this may be compared to the classification based on the visible light in step 602. For example, a classification accuracy value of around 80% may be produced as a result of the comparison.

At step 606, the video system 30 determines whether the classification accuracy value is above a predetermined threshold. In a case where the classification accuracy value is above a predetermined threshold, at step 608, the video system 30 generates a first bounding box around the detected object. For example, the predetermined threshold for the classification accuracy value may be around 60%. Comparing the 80% classification accuracy value in the example, to the 60% threshold, the video system 30 would determine that the classification accuracy value is higher than the threshold of 60%.

At step 610, the video system 30 generates a first augmented view of the image based on the classification. The augmented view may include the bounding box around the object and a tag indicating the classification. For example, the augmented view may display a tag for the instrument as a bipolar grasper near the instrument.

At step 612, the video system 30 displays the augmented image on a display. In various embodiments, the video system 30, in a case where the classification accuracy value is below the predetermined threshold, may further cause the system to display on the display an indication that the classification accuracy value is not within an expected range. In various embodiments, the augmented view further includes an indication of the classification accuracy value.

Figure 7:
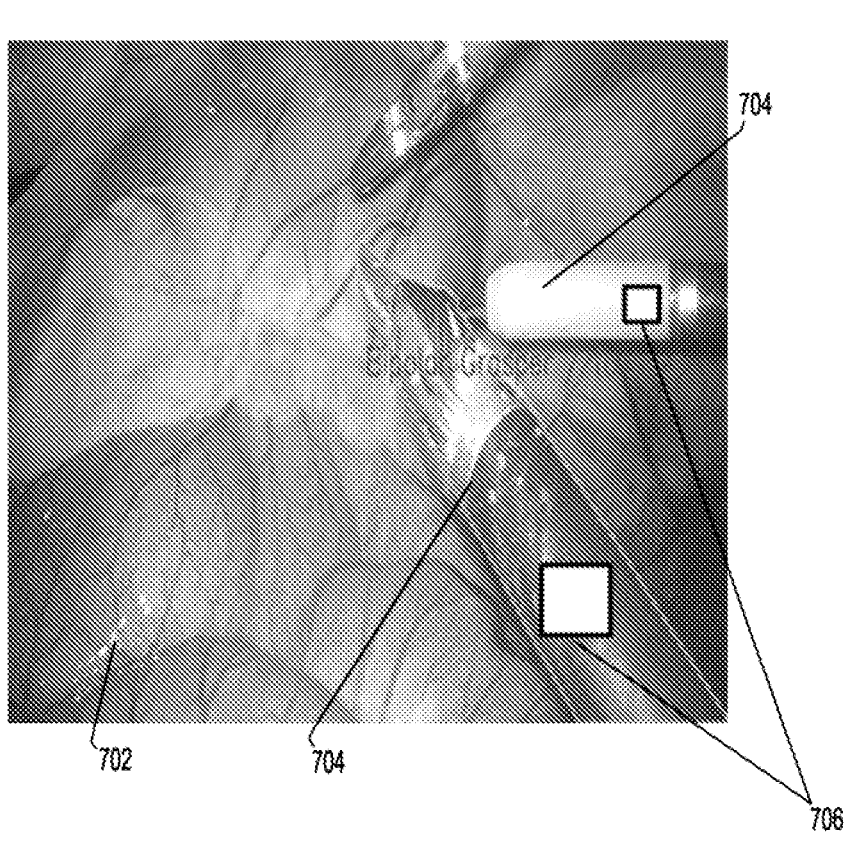
FIG. 7 is an exemplary input image including a surgical operative site in accordance with the disclosure.

With reference to FIG. 7, an exemplary input image 700 including a surgical operative site in accordance with the disclosure is shown. The input image 700 may include tissue 702 being operated on with a surgical tool 704. The surgical tool 704 may include an IR marking 706 on the shaft or on the jaws of the surgical tool 704. The IR marking 706 would remain invisible to the user of the endoscope system 1. However, the IR markings 706 would be detected by the image sensor 32 of endoscope system 1 and may be used for surgical tool 704 identification.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the disclosure. Various alternatives and modifications can be devised by those skilled in the art without departing from the disclosure. Accordingly, the disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for object identification in endoscopy images, comprising:

a light source configured to provide light within a surgical operative site, the light source configured to simultaneously or alternatively produce a first light including an infrared (IR) band and a second light including a visible band;

an imaging device configured to acquire images from the surgical operative site;

an imaging device control unit configured to control the imaging device, the control unit including:

a processor; and a memory storing instructions thereon, which, when executed by the processor, cause the system to:

provide, from the light source, light within the surgical operative site including at least one of the first light or the second light;

switch the light source to produce only the first light;

capture an image of an object located in the surgical operative site, by the imaging device, the image including only the first light from the object, the object including an infrared (IR) marking applied to the object, the IR marking including data corresponding to information about a type of the object;

access the image;

perform real-time image recognition on the image to detect the IR marking;

perform real-time image recognition on the image to detect the object and classify the object, based on the IR marking applied to the object;

generate an augmented image where the IR marking is removed from the image; and display the augmented image on a display.

2. The system of claim 1, wherein performing real-time image recognition, based on the IR marking, includes amplifying the IR marking.

3. The system of claim 2, wherein the instructions, when executed, further cause the system to:

perform real-time image recognition on the image to detect the object and classify the object, based on the second light when the light source produces the second light; and compare the object classification based on the amplified IR marking and the object classification based on the second light to produce a classification accuracy value;

in a case where the classification accuracy value is above a predetermined threshold:

generate a first bounding box around the detected object;

generate a first augmented view of the image based on the classification, the augmented view including the bounding box and a tag indicating the classification; and display the augmented image on a display.

4. The system of claim 3, wherein in a case where the classification accuracy value is below the predetermined threshold, the instructions, when executed, further cause the system to display on the display an indication that the classification accuracy value is not within an expected range.

5. The system of claim 4, wherein the augmented view further includes an indication of the classification accuracy value.

6. The system of claim 1, wherein the IR marking includes a pattern that indicates a data bit and an error checking bit.

7. The system of claim 6, wherein the data bit indicates at least one of a surgical tool type or a surgical tool feature.

8. The system of claim 1, wherein the instructions, when executed, further cause the system to:

perform tracking of the detected object based on the IR marking.

9. The system of claim 1, wherein the instructions, when executed, further cause the system to:

adjust a control parameter of the system based on the detected object.

10. The system of claim 1, wherein the IR marking includes at least one of a logo, a two-dimensional code, a texture, a dot pattern, or a unique identifier.

11. A method of object identification in endoscopy images, comprising:

providing light within a surgical operative site including at least one of a first light including an infrared (IR) band or a second light including a visible band;

switching the light source to produce only the first light;

capturing an image of an object within the surgical operative site, by an imaging device, the image including only the first light radiating from the object, the object including an infrared (IR) marking applied to the object, the IR marking including data corresponding to information about a type of the object;

accessing the image;

performing real-time image recognition on the image to detect the IR marking;

performing real-time image recognition on the image to detect the object and classify the object, based on the IR marking applied to the object;

generating an augmented image where the IR marking is removed from the image; and displaying the augmented image on a display.

12. The method of claim 11, wherein the performing real-time image recognition on the image to detect the IR marking includes amplifying the IR marking.

13. The method of claim 12, the method further comprising:

performing real-time image recognition on the image to detect the object and classify the object, based on the second light when the light source produces the second light; and comparing the object classification based on the amplified IR marking and the object classification based on the second light to produce a classification accuracy value;

in a case where the classification accuracy value is above a predetermined threshold:

generating a first bounding box around the detected object;

generating a first augmented view of the image based on the classification, the augmented view including the bounding box and a tag indicating the classification; and displaying the augmented image on a display.

14. The method of claim 13, wherein in a case where the classification accuracy value is below the predetermined threshold, displaying on the display an indication that the classification accuracy value is not within an expected range.

15. The method of claim 14, wherein the augmented view further includes an indication of the classification accuracy value.

16. The method of claim 15, wherein the method further comprises performing tracking of the detected object based on the detected object based on the IR marking.

17. The method of claim 11, wherein the IR marking includes at least one of a logo, a two-dimensional code, a texture, a dot pattern, or a unique identifier.

18. The method of claim 11, wherein the IR marking includes a pattern that indicates a data bit and an error checking bit.

19. The method of claim 18, wherein the data bit indicates a surgical tool type.

20. A non-transitory storage medium that stores a program causing a computer to execute a computer-implemented method of object identification in endoscopy images, the computer-implemented method comprising:

providing light within a surgical operative site including at least one of a first light including an infrared (IR) band or a second light including a visible band;

switching the light source to produce only the first light;

capturing an image of an object, by an imaging device, the image including only the first light radiating from the object, the object including an infrared (IR) marking applied to the object, the IR marking including data corresponding to information about a type of the object;

accessing the image;

performing real time image recognition on the image to detect the IR marking;

performing real time image recognition on the image to detect the object and classify the object, based on the IR marking applied to the object;

generating an augmented image where the IR marking is removed from the image; and displaying the augmented image on a display.

\* \* \* \* \*